United States Patent
Naddaka et al.

(10) Patent No.: US 7,524,960 B2
(45) Date of Patent: Apr. 28, 2009

(54) HIGHLY PURE CILOSTAZOL AND AN IMPROVED PROCESS FOR OBTAINING SAME

(75) Inventors: Vladimir Naddaka, Lod (IL); Guy Davidi, Even-Yehuda (IL); Shady Saeed, Haifa (IL); Oded Arad, Rechovot (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 440 days.

(21) Appl. No.: 11/080,460

(22) Filed: Mar. 16, 2005

(65) Prior Publication Data

US 2005/0222202 A1 Oct. 6, 2005

Related U.S. Application Data

(60) Provisional application No. 60/553,140, filed on Mar. 16, 2004.

(51) Int. Cl.
*C07D 215/38* (2006.01)
(52) U.S. Cl. ..................................... 546/158
(58) Field of Classification Search ................. 546/158
See application file for complete search history.

(56) References Cited

U.S. PATENT DOCUMENTS

| | | | |
|---|---|---|---|
| 4,277,479 A * | 7/1981 | Nishi et al. ................. | 514/312 |
| 6,187,790 B1 | 2/2001 | Cutler | |
| 6,388,080 B1 * | 5/2002 | Stowell et al. .............. | 546/155 |
| 6,515,128 B2 * | 2/2003 | Mendelovici et al. ....... | 546/158 |
| 6,525,201 B2 * | 2/2003 | Mendelovici et al. ....... | 546/158 |
| 6,657,061 B2 * | 12/2003 | Stowell et al. .............. | 546/158 |
| 6,740,758 B2 * | 5/2004 | Mendelovici et al. ....... | 546/158 |
| 6,825,214 B2 | 11/2004 | Mendelovici et al. | |
| 7,026,486 B2 * | 4/2006 | Yamamoto et al. .......... | 546/158 |
| 7,060,833 B2 * | 6/2006 | Mendelovici et al. ....... | 546/158 |
| 2003/0045547 A1 | 3/2003 | Aki et al. | |
| 2004/0024017 A1 | 2/2004 | Aki et al. | |

OTHER PUBLICATIONS

Nishi, CA 99:98806, abstract of Chem & Pharm Bull, vol. 31(4), pp. 1151-1157, 1983.*
Nishi et al. "Studies on 2-Oxoquinoline Derivatives as Blood Platelet Aggregation Inhibitors. II. 6-[3-(1-Cyclohexyl-5-Tetrazolyl) Propoxy]-1,2-Dihydro-2-Oxoquinoline and Related Compounds", Chem. Pharmaceut. Bulletin, 31(4): 1151-1157, 1983.

* cited by examiner

*Primary Examiner*—D. Margaret Seaman

(57) ABSTRACT

A novel process for preparing highly pure cilostazol, effected by reacting 6-hydroxy-3,4-dihydroquinolinone and 5-(4-chlorobutyl)-1-cyclohexyl-1H-tetrazole in the presence of a hydrated inorganic base, is disclosed. Further disclosed is highly pure cilostazol, and particularly highly pure cilostazol that is substantially free of 6-[4-(1-cyclohexyl-1H-tetrazol-5-yl)-butoxy]-1-[4-(1-cyclohexyl-1H-tetrazol-5-yl)-butyl]-3,4-dihydro-1H-quinolin-2-one.

24 Claims, 5 Drawing Sheets

HIGHLY PURE CILOSTAZOL AND AN IMPROVED PROCESS FOR OBTAINING SAME

This application claims the benefit of priority from U.S. Provisional Patent Application No. 60/553,140, filed Mar. 16, 2004.

FIELD AND BACKGROUND OF THE INVENTION

The present invention relates to the field of chemistry, and more particularly to a novel and improved process of preparing 6-(4-(1-cyclohexyl-1H-tetrazol-5-yl)butoxy)-3,4-dihydro-2(1H)-quinolinone (also known under the generic name cilostazol), and to highly pure cilostazol.

6-(4-(1-cyclohexyl-1H-tetrazol-5-yl)butoxy)-3,4-dihydro-2(1H)-quinolinone (also known and referred to herein as Cilostazol), is known as an inhibitor of cell platelet aggregation. Cilostazol is presently marketed (under the brand name Pletal™ by Otsuka American Pharmaceutical, Inc. of Rockville, Md.) as a drug for the treatment of stable intermittent claudication.

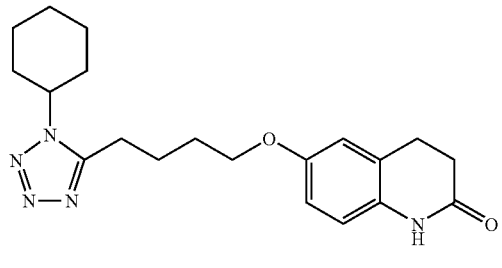

Cilostazol

Intermittent claudication is a condition caused by narrowing of the arteries that supply the legs with blood. Patients with intermittent claudication suffer from oxygen deficiency in the blood vessels that reach the active leg muscles and thus develop a severe pain, aching or cramping in the legs during walk. This medical condition is typically caused by a peripheral atherosclerotic vascular disease; a condition more commonly known as atherosclerosis or hardening of the arteries. Atherosclerosis occurs when deposits of fatty substances build up, in this case in the legs, leading to an inadequate blood supply to the leg muscles. Intermittent claudication affects tens of million of, predominantly, elderly people. It can greatly impair their ability to walk without considerable discomfort and can seriously affect their ability to exercise or even engage in ordinary activities of daily life.

The presently standard effective treatments of intermittent claudication include intensive exercise regimens, drug treatments, such as pentoxifylline (Trental™) and Cilostazol, and under certain circumstances, re-vascularization surgical procedures (operations to open the leg arteries or provide a replacement artery).

Administration of cilostazol to subjects suffering from intermittent claudication dilates the arteries and thereby improves blood and oxygen supply to the legs, enabling faster and prolonged leg motion. Patients treated with cilostazol reported substantial improvement in both walking distance and walking speed during daily routines.

The mechanism of action of cilostazol is yet unclear. Cilostazol is known as an inhibitor of phosphodiesterase III (PDE III), and as a result exerts vasodilation and inhibition of platelet aggregation activities. Nevertheless, it is not clear whether its beneficial effect on intermittent claudication is attributed to these activities Cilostazol is now being studied for its use as a therapeutic agent for various indications other than intermittent claudication, such as sexual dysfunctions and additional medical conditions related to blood circulation (see, for example, U.S. Pat. No. 6,187,790).

The synthesis of cilostazol was first described in U.S. Pat. No. 4,277,479 (to Otsuka Pharmaceutical Co.). According to the teachings of this patent, cilostazol and analogs thereof are prepared by a process that involves alkylation of a hydroxycarbostyril derivative, having the general Formula I below, with a tetrazole derivative, having the general Formula II below, wherein X represents a halogen atom and n represents the length of the hydrocarbon chain connecting the tetrazole and the halogen atom (see, Scheme 1 below).

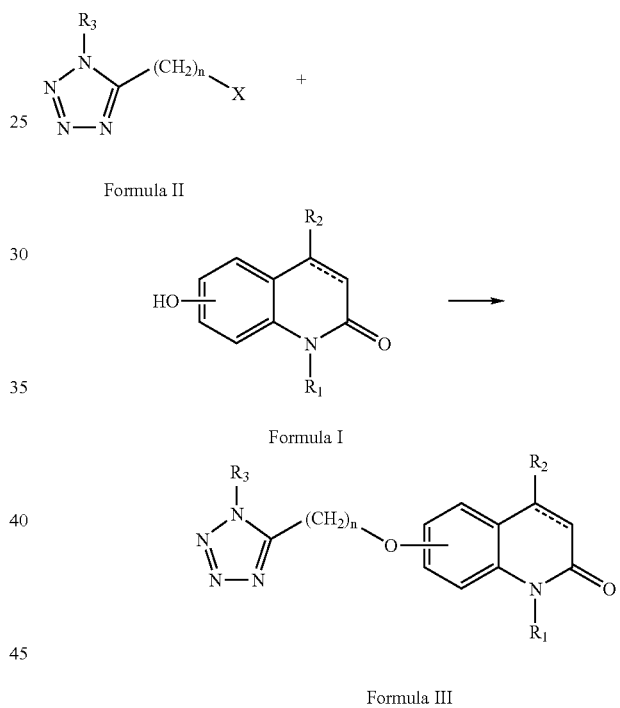

According to the teachings of U.S. Pat. No. 4,277,479, the above reaction is performed at conventional alkaline conditions, using a wide variety of organic and inorganic bases, and in the absence or presence of an inert solvent.

Thus, further according to the teachings of U.S. Pat. No. 4,277,479, cilostazol is prepared from 6-hydroxy-3,4-dihydroquinolinone (also referred to herein throughout as Compound I) and a molar excess of 5-(4-chlorobutyl)-1-cyclohexyl-1H-tetrazole (also referred to herein throughout as Compound II) using 1,8-diazabicyclo[5,4,0]undec-7-ene (DBU) as a base and ethanol as a solvent.

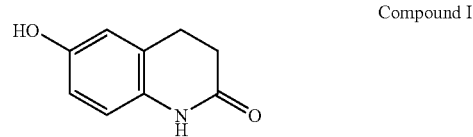

Compound I

Compound II

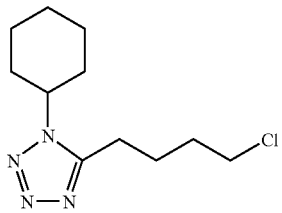

Later on, Nishi, et al. (*Chem. Pharm. Bull.*, 31, 1983, 1151-57), described a method of preparing Cilostazol in a higher yield of 74%, by reacting Compound I with a molar excess of Compound II in isopropanol in the presence of potassium hydroxide as a base, and purifying the resulting product by column. chromatography and recrystallization from methanol.

Additional processes for preparing cilostazol are taught in U.S. Pat. No. 6,515,128 and its continuation-in-part U.S. Pat. No. 6,825,214 (to Teva Pharmaceutical Industries Ltd.).

One of these processes involves a phase transfer reaction of Compound I with Compound II in a mixture of a water-immiscible solvent and water in the presence of a water-soluble base, and a quaternary ammonium phase transfer catalyst. The most preferred quaternary ammonium phase transfer catalyst, according to the teachings of these patents, is tricaprylylmethylammonium chloride (Aliquate®336). This process further involves isolation of crude cilostazol from the biphasic mixture and its purification by recrystallization.

The second process involves a reaction of Compound I with a molar excess of Compound II in a non-aqueous hydroxylic solvent, such as 1-butanol, 2-propanol, 2-butanol and amyl alcohol, in the presence of an alkali metal hydroxide, such as potassium hydroxide, and an alkali metal carbonate, such as potassium carbonate. This process further involves isolation of crude cilostazol from the reaction. mixture and its purification by recrystallization.

The third process involves a reaction of Compound I with Compound II in a non-aqueous hydroxylic solvent in the presence of a mixture of an alkali metal hydroxide and an alkali metal carbonate as base, and molecular sieves as an agent of dehydration. This process further involves isolation of crude cilostazol from the reaction mixture and its purification by recrystallization.

The inventors of the present invention reproduced the abovementioned, processes (see, Reference Examples 1-7 in the Examples section hereinbelow), and used HPLC measurements to analyze the composition of the reaction mixture after each step, and to thereby meticulously follow and detect any trace amount of an impurity. The inventors of the present invention have thus uncovered that a substantial amount of the impurity 6-[4-(1-cyclohexyl-1H-tetrazol-5-yl)-butoxy]-1-[4-(1-cyclohexyl-1H-tetrazol-5yl)-butyl]-3,4-dihydro-1H-quinolin-2-one (also referred to herein throughout as Compound III, presented hereinbelow) is present in the final product (both the crude and purified cilostazol) obtained by all of these processes (see, for example, FIGS. 1-3). The presence of such an impurity was not reported in any of the abovementioned prior art processes. The present inventors have further found that the most substantial amounts of this impurity are obtained in processes which involve inorganic bases (see, for example, Reference Examples 2, 4, 6 and 7 hereinbelow and FIGS. 1-3).

Compound III

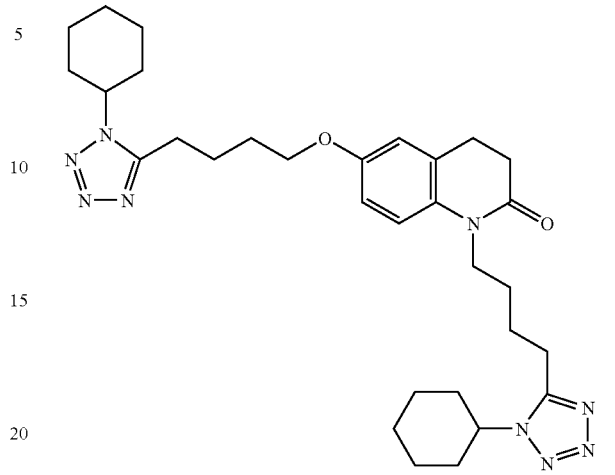

The formation of Compound III as a substantial impurity obtained along with the desired product cilostazol is highly undesirable and pauses a major limitation to the entire synthesis process, particularly due to the findings that such an impurity is exceptionally difficult to remove from the final product by methods suitable for commercial scale (such as recrystallization) and hence may require the use of column chromatography.

Thus, while the prior art teaches several processes for preparing cilostazol, all of these processes are limited in that they require the use of excessive amounts of at least one of the starting materials in order to achieve acceptable reaction yields, and/or the use of reagents which are hazardous, expensive and/or difficult to isolate and remove from the reaction product and/or involve the formation of substantial amounts of Compound III.

As is mentioned above, some of the processes described hereinabove for preparing cilostazol use an excessive amount of at least one of the starting materials. The starting materials typically used in the synthesis of cilostazol, namely, 5-(4-chlorobutyl)-1-cyclohexyl-1H-tetrazole and 6-hydroxy-3,4-dihydroquinolin-2(1H)-one, are expensive compounds. In general, the need to use of molar excess of any of the starting materials, and/or of any expensive reagent, typically indicates that the reaction conditions are less than optimal in terms of yields, impurities and the treatment of waste. Therefore an improved process that would allow an efficient use of the starting materials is critical in the commercial scale production of cilostazol.

In addition, processes which involve the use of organic bases, such as 1,8-diazabicyclo[5,4,0]undec-7-ene (DBU), are limited due to the hazardousness of these compounds (DBU, for example, is classified as a harmful substance that may cause burns and lachrymation) and the difficulties encountered while trying to isolate these compounds from the product mixture, which oftentimes lead to use column chromatography or repetitive purification procedures. Similarly, processes in which a phase transfer catalyst, such as the reagent Aliquat®336, is used are limited by the acute hazardousness of this catalyst (Aliquate®336 is classified as a highly toxic substance by inhalation, ingestion or skin absorption, a severe irritant and very destructive of mucous membranes), and the difficulties encountered during purification of the product. Phase transfer catalysts are also oftentimes costly and environmentally unfriendly.

Processes that involve the use of inorganic bases are relatively advantageous in this respect. Inorganic bases are relatively inexpensive, are easy to handle, are relatively environmentally friendly and, most advantageously, can readily be separated from the final product. However, as mentioned above, the present inventors have uncovered that the processes described in the art which use inorganic bases for the synthesis of cilostazol, are severely limited by the substantial formation of Compound III.

There is thus a widely recognized need for, and it would be highly advantageous to have an efficient process for preparing cilostazol devoid of the above limitations.

SUMMARY OF THE INVENTION

In a search for an improved process for preparing cilostazol, which would be devoid of the limitations described above, the present inventors have designed and successfully practiced a novel process for preparing cilostazol. The novel process described herein results in highly pure cilostazol, and particularly in cilostazol which is free of impurities that are exceptionally difficult to remove from the final product, such as Compound III described above. The novel process of the present invention is also highly efficient in terms of chemical yields, and is cost effective, simple to perform and safe.

Thus, according to one aspect of the present invention, there is provided 6-(4-(1-cyclohexyl-1H-tetrazol-5-yl)butoxy)-3,4-dihydro-2(1H)-quinolinone (Cilostazol) that is substantially free of N-[4-(1-cyclohexyl-1H-tetrazol-5-yl)butyl]-6-[4-(1-cyclohexyl-1H-tetrazol-5-yl)butoxy]-3,4-dihydro-2(1H)-quinolinone (Compound III).

According to further features in preferred embodiments of the invention described below, the cilostazol has a purity that equals to or is greater than 99.5%, and preferably a purity that equals to or is greater than 99.9%.

According to still further features in the described preferred embodiments, the content of Compound III is less than 0.1 weight percent.

According to another aspect of the present invention there is provided a process of preparing cilostazol, the process comprising:

providing 6-hydroxy-3,4dihydroquinolin-2(1H)-one (Compound I);

providing 5-(4chlorobutyl)-1-cyclohexyl-1H-tetrazole (Compound II);

reacting Compound I and Compound II in the presence of a hydrated inorganic base, to thereby obtain a reaction mixture containing cilostazol; and isolating the cilostazol from the reaction mixture.

According to further features in preferred embodiments of the invention described below, According to further features in preferred embodiments of the invention described below, the molar ratio between Compound I and Compound II ranges between about 1:1 and about 2:1. Preferably the molar ratio is about 1.3:1.

According to still further features in the described preferred embodiments the cilostazol obtained by the process described above is substantially free of Compound III. Preferably the thus obtained cilostazol contains less than 0.1 weight percent of Compound III, and more preferably less than 0.06 weight percent.

According to still further features in the described preferred embodiments the crude cilostazol obtained by the process described above has a purity that equals to or is greater than 99.5%.

According to still further features in the described preferred embodiments the hydrated inorganic base used in the process contains at least 5 weight percentages of water, preferably at least 10 weight percentages of water, and more preferably at least 15 weight percentages of water. The inorganic base can be, for example, sodium hydroxide, potassium hydroxide, sodium carbonate, potassium carbonate, sodium bicarbonate and potassium bicarbonate, and preferably potassium hydroxide.

According to still further features in the described preferred embodiments the molar ratio between the hydrated inorganic base and Compound II ranges between about 1:1 and about 2:1, and preferably, the molar ratio is about 1.2:1.

According to still further features in the described preferred embodiments the reaction between Compound I and Compound II is performed in an organic solvent such as, but not limited to, methanol, ethanol, 1-propanol, 2-propanol, 1-butanol, 2-butanol and any combinations thereof. Preferably the organic solvent is 1-propanol.

According to still further features in the described preferred embodiments the reaction solvent contains water.

According to still further features in the described preferred embodiments the reaction solvent is a mixture of 1-propanol and water, at a 1-propanol to water ratio that ranges from 20:1 to 1:1 and is preferably 18:1.

According to still further features in the described preferred embodiments the reaction is performed at reflux temperature of the solvent.

According to still further features in the described preferred embodiments the isolation of the crude cilostazol is effected by precipitating the cilostazol from the reaction mixture at a temperature lower than 15° C.

According to still further features in the described preferred embodiments the process according to this aspect of the present invention further includes purifying the cilostazol.

According to still further features in the described preferred embodiments the purification is effected by slurrying the obtained cilostazol in a first organic solvent; and/or recrystallizing the obtained cilostazol from a mixture containing a second organic solvent and an aqueous solution of an inorganic base.

According to still further features in the described preferred embodiments the purification includes both the slurrying and the recrystallization described herein. In one preferred embodiment, the slurrying step precedes the recrystallization step, and in another preferred embodiment the recrystallization step precedes the slurrying step.

According to still further features in the described preferred embodiments the first organic solvent used in the slurrying is ethyl acetate.

According to still further features in the described preferred embodiments the second organic solvent used in the recrystallization is 1-propanol. The aqueous solution of an inorganic base used is preferably an aqueous solution of sodium. hydroxide.

According to still further features in the described preferred embodiments the cilostazol obtained in the process described above is substantially free of Compound III and is highly pure.

Hence, according to the still another aspect of the present invention there is provided cilostazol having a purity that equals to or is greater than 99.9%.

The present invention successfully addresses the shortcomings of the presently known configurations by providing an improved process of preparing cilostazol, which results in highly pure cilostazol substantially free of undesired impurities such as Compound III.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used in this application, the singular form "a", "an" and "the" include plural references unless the context clearly dictates otherwise. For example, the term "an agent" includes a plurality of agents, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3 from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein throughout the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause, of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
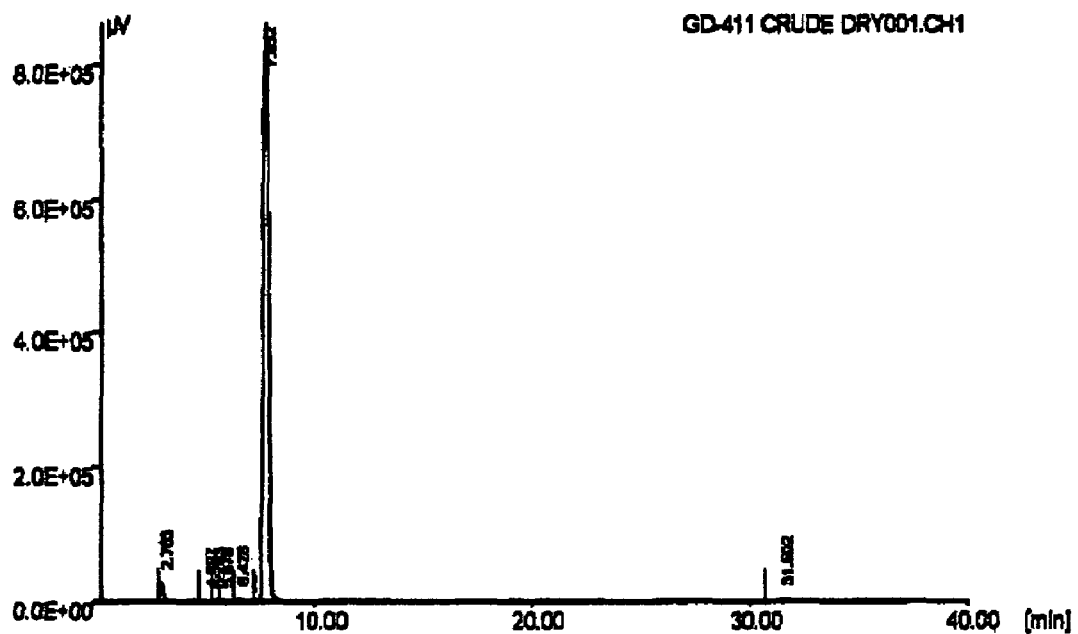
FIG. 1 presents an HPLC chromatogram of the crude product obtained by reproducing the process described in Example 2 of U.S. Pat. Nos. 6,515,128 and 6,825,214 (see, Reference Example 4 hereinunder), which indicates that the crude product contains 1.649% of Compound I (retention time 2.763 minutes, area=160042.649), 0.051%, 0.042%, 0.125% and 0.232% of unidentified impurities (having retention times at 4.887, 5.283, 5.678 and 6.428 minutes, respectively), 97.060% of cilostazol (retention time 7.652 minutes, area=9418407.067) and 0.840% of Compound III (retention time 31.502 minutes, area=81554.703), whereby the total peak area is 9703713.818 [µV.sec]

The present invention is of a novel process for the preparation of 6-(4-(1-cyclohexyl-1H-tetrazol-5-yl)butoxy)-3,4di-hydro-2(1H)-quinolinone (cilostazol), which results in highly pure cilostazol, and particularly is cilostazol free of impurities that are exceptionally difficult to remove from the final product, such as N-[4-(1-cyclohexyl-1H-tetrazol-5-yl)butyl]-6-[4-(1-cyclohexyl-1H-tetrazol-5-yl)butoxy]-3,4-dihydro-2(1H)-quinolinone (Compound III). The novel process of the present invention is also highly efficient in terms of chemical yields, and is cost effective, simple to perform and safe.

The principles and operation of the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments of being practiced or carried out in various ways. Also, it is to be understood that the phraseology and terminology employed herein is for the purpose of description and should not be regarded as limiting.

As is described hereinabove, the presently known processes of preparing Cilostazol, as taught in U.S. Pat. Nos. 4,277,479, 6,515,128, 6,825,214 and in Nishi, et al., *Chem. Pharm. Bull.*, 31, 1983, 1151-57, suffer from one or more of the following limitations: chemical inefficiency which leads to the use of excessive amounts of the starting materials (6-hydroxy-3,4-dihydroquinolin-2(1H)-one (Compound I) and 5-(4-chlorobutyl)-1-cyclohexyl-1H-tetrazole (Compound II)); formation of impurities which are outstandingly non-detectable and are hard to remove from the final product; and the use of expensive, hazardous and hard to remove reagents, such as 1,8-diazabicyclo[5,4,0]undec-7-ene (DBU) and the phase transfer catalyst Aliquat®336.

As is described hereinabove, while reproducing the processes described in the abovementioned references (see, Reference Examples 1-7 in the Examples section that follows), the present inventors surprisingly uncovered, during an HPLC analysis of the products, that substantial amounts of 6-[4-(1-cyclohexyl-1H-tetrazol-5-yl)-butoxy]-1-[4-(1-cyclohexyl-1H-tetrazol-5-yl)-butyl]-3,4-dihydro-1H-quinolin-2-one (see, Compound III above) are formed during these processes, and are thus present in the final Cilostazol product obtained by these processes. Exemplary HPLC chromatograms of a product obtained by one of these prior art processes, in which the presence of Compound III is clearly shown are presented in FIGS. 1-3.

The formation of Compound III as a substantial impurity obtained along with the desired product cilostazol is highly undesirable and pauses a major limitation, to the entire synthesis process, particularly due to the findings that such an impurity is exceptionally difficult to remove from the final product by methods suitable for commercial scale (such as recrystallization) and hence may require the use of the laborious column chromatography or repetitive purification procedures.

The present inventors have also uncovered that particularly high levels of this impurity are formed in the processes that involve inorganic bases. Thus, although such processes appear to be the most advantageous due to the cost-efficiency, availability and safety of such bases, the presence of such an impurity limit the efficiency thereof.

Figure 2:
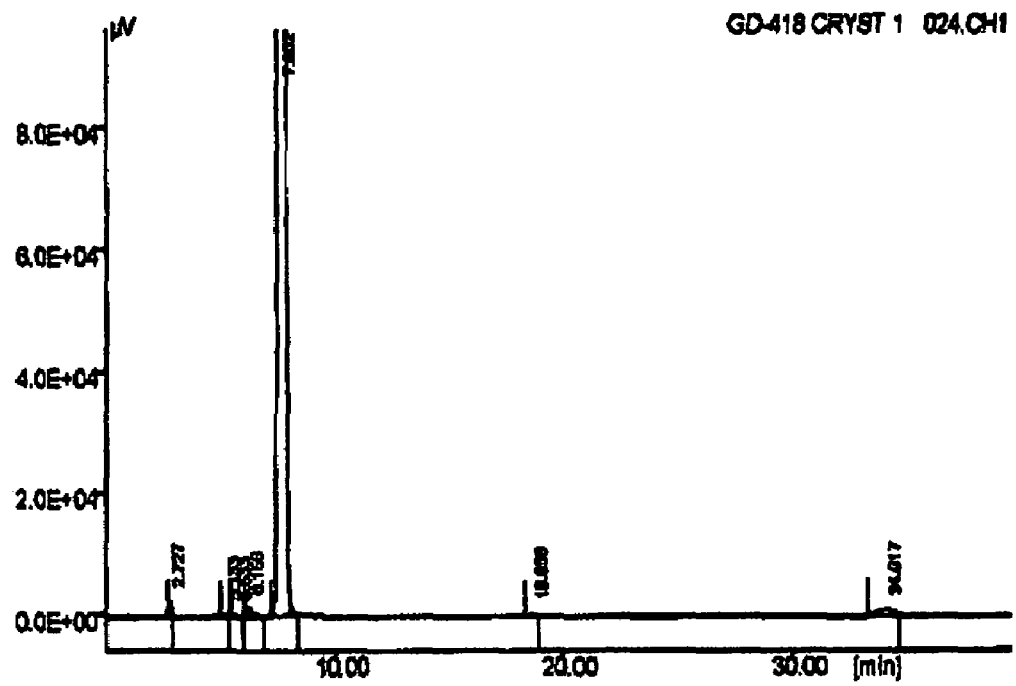
FIG. 2 presents an HPLC chromatogram of a recrystallized product obtained by reproducing the process described in Example 2 of U.S. Pat. Nos. 6,515,128 and 6,825,214 (see, Reference Example 4 hereinunder), which indicates that the recrystallized product contains 0.117% of Compound I (retention time 2.727 minutes, area=13583.000), 0.016%, 0.029% and 0.129% of unidentified impurities (having retention times at 5.133, 5.533 and 6.158 minutes, respectively), 99.436% of cilostazol (retention time 7.602 minutes, area=11534984.999). 0.014% of an impurity (retention time 18.658 minutes) and 0.258% of Compound III (retention time 34.017 minutes, area=29965.129), whereby the total peak area is 11600372.909 [µV.sec]
Figure 3:
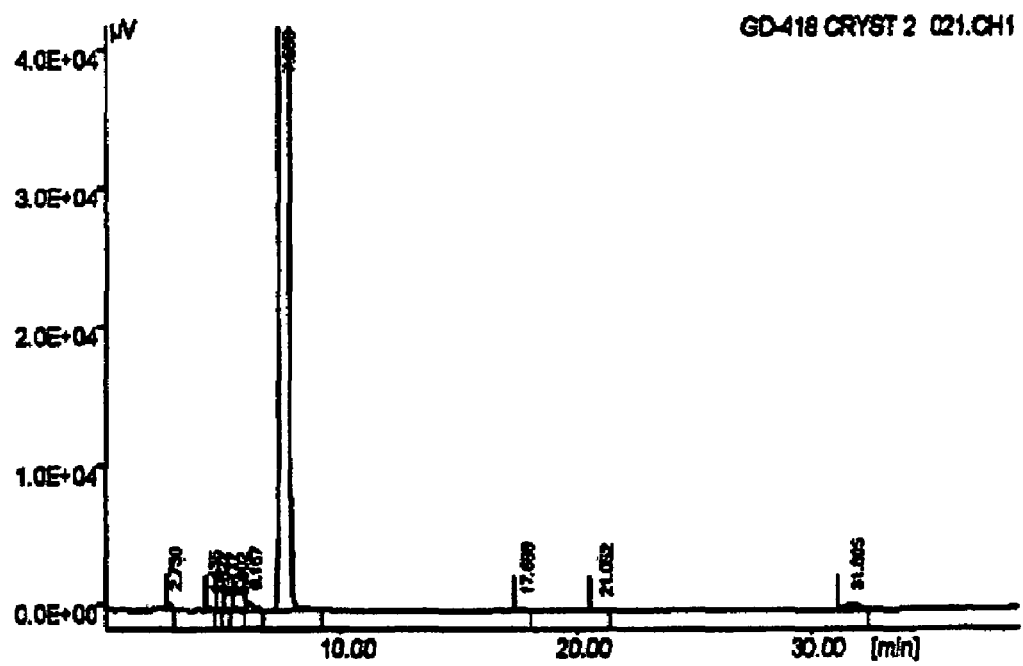
FIG. 3 presents an HPLC chromatogram of the re-recrystallized product obtained by reproducing the process described in Example 2 of U.S. Pat. Nos. 6,515,128 and 6,825,214 (see, Reference Example 4 hereinunder), which indicates that the re-recrystallized product contains 0.030% of Compound I (retention time 2.730 minutes, area=2373.517), 0.018%, 0.012%, 0.017%, 0.027% and 0.119% of unidentified impurities (having retention times at 4.435, 4.822, 5.177, 5.602 and 6.157 minutes, respectively), 99.523% of cilostazol (retention time 7.568 minutes, area=7767929.179), 0.034% of an impurity (retention time 17.688 minutes), 0.016% of another impurity (retention time 21.052 minutes) and 0.204% of Compound III (retention time 31.805 minutes, area=15917.288), whereby the total peak area is 7805168.510 [µV.sec]

As is detailed in the examples section that follows, while performing HPLC measurements for analyzing the contents of the obtained cilostazol, it was found that the impurity Compound III has a relatively high retention time of about 30 minutes (see, for example, Reference Example 4 and FIGS. 1-3). It may therefore be assumed that the while practicing the abovementioned prior art processes for preparing cilostazol, the presence of such an impurity was not uncovered and therefore no motivation to design and practice a process in which the presence of this impurity would be at least minimized if not circumvented was provided heretofore.

While studying the formation of Compound III during the process of preparing cilostazol, and based on the above findings and common knowledge, it was postulated that Compound III is formed by a reaction between the cilostazol formed in the process and Compound II, as is illustrated in Scheme 2 below.

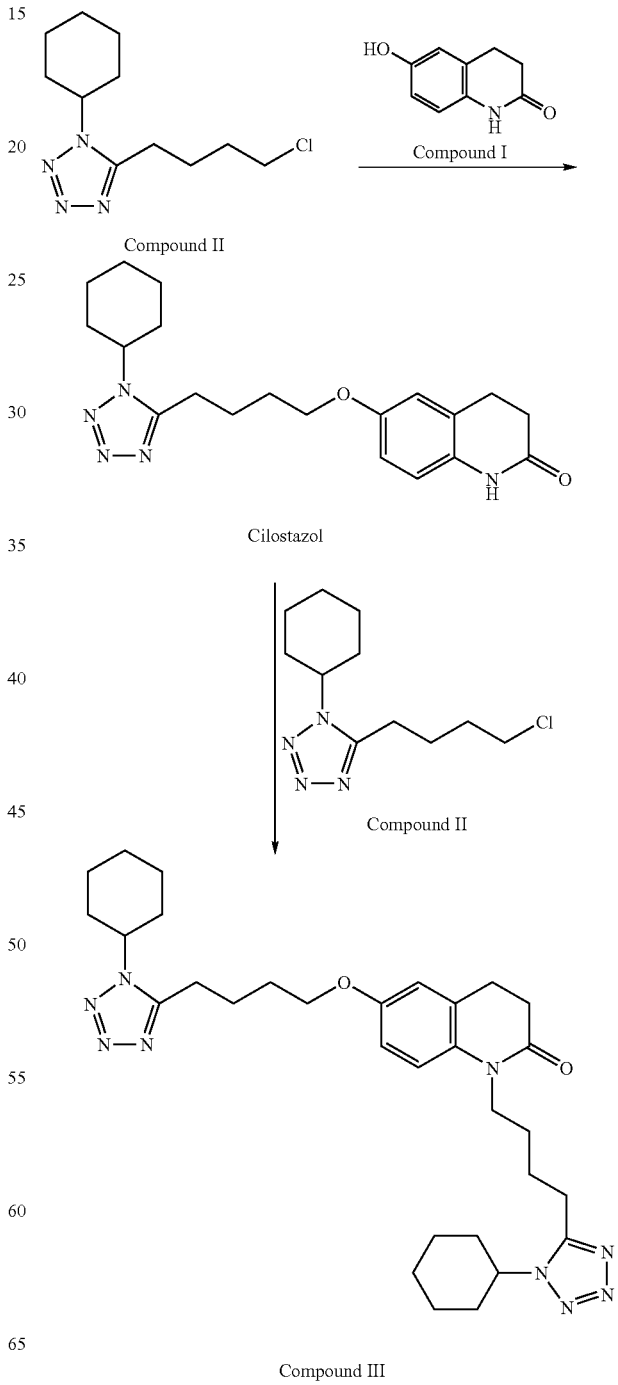

Scheme 2

The formation of Compound III therefore further adversely affects the overall yield of the process by depleting both, the expensive starting material Compound II and the obtained cilostazol, toward the formation of Compound III. The exemplary HPLC chromatograms presented in FIGS. 1-3 reveal the composition of the product after each step of the above-mentioned prior art process disclosed in Example 2 of U.S. Pat. Nos. 6,515,128 and 6,825,214 (see, Reference Example 4 below). These chromatograms clearly show a persistent peak representing Compound III, a peak for the starting material, Compound I, and no peak for Compound II. These observations support the postulate of the present inventors for the formation of Compound III and its relation to the shortcomings of the prior art processes.

In a search for an improved process of preparing Cilostazol, which would be free of the impurity of Compound III, while maintaining efficient use of the starting materials and highly pure final product, the present inventors have studied the conditions which lead to the formation of Compound III. During these studies, the present inventors have uncovered (see, Example 4 in the Examples section that follows) that favorable conditions for the formation of Compound III include the presence of an inorganic base under anhydrous conditions.

Thus, while conceiving the present invention, it was envisioned that performing a process of preparing cilostazol in the presence of an inorganic base and non-anhydrous conditions would result in higher yield and purity of the product, with minimal formation of Compound III.

As is demonstrated in the Examples section that follows (see, Examples 1-3), while reducing the present invention to practice, the present inventors have designed and successfully practiced a novel process of preparing cilostazol, which is generally effected by reacting Compound I and Compound II in the presence of a hydrated inorganic base and optionally in the presence of a mixture or an organic solvent and water as the reaction medium. The present inventors have further designed and successfully practiced a purifying procedure which allows the removal of even a trace amount of Compound III, as well as of any other detectable impurity. This novel process is highly advantageous as it results in the formation of substantially pure cilostazol, having a purity that equals to or is greater than 99.9%, that is further substantially free of Compound III.

All impurity content and purity levels indicated herein were determined by HPLC analysis. An exemplary protocol for an HPLC analysis is presented in the Examples section which follows.

Hence, according to one aspect of the present invention, there is provided a process of preparing cilostazol, which is effected by providing 6-hydroxy-3,4-dihydroquinolin-2 (1H)-one (herein, Compound I); providing 5-(4-chlorobutyl)-1-cyclohexyl-1H-tetrazole (herein, Compound II); reacting Compound I and Compound II in the presence of a hydrated inorganic base, to thereby obtain a reaction mixture containing cilostazol; and isolating the cilostazol from the reaction mixture.

According to a preferred embodiment of this aspect of the present invention, the hydrated inorganic base contains at least 5 weight percentages of water. More preferably, the hydrated inorganic base contains at least 10 weight percentages of water, and most preferably, the hydrated inorganic base contains at least 15 weight percentages of water.

As used herein throughout, the term "weight percentage(s)" or "weight percent(s)" describes the weight percentage(s) of an ingredient of the total weight of a substance, mixture or composition containing the ingredient.

Representative examples of inorganic bases that are suitable for use in this process according to the present invention include, without limitation, sodium hydroxide, potassium hydroxide, sodium carbonate, potassium carbonate, sodium bicarbonate and potassium bicarbonate.

The inorganic base can be used in the process of the present invention in any acceptable and commercially available form thereof, including a powder, pellets, flakes, granules, crystals, grains and flocks.

As is demonstrated in the Examples section that follows, exceptional results were obtained using potassium hydroxide, in the form of a powder or flakes, as the inorganic base.

The amount of the inorganic base used in this process is preferably selected such that the molar ratio between the hydrated inorganic base and Compound II ranges between about 1:1 and about 2:1. In a preferred embodiment of the present invention, the molar ratio between the hydrated inorganic base and Compound II is about 1.2:1.

As used herein the term "about" refers to ±10%.

According to another preferred embodiment of the process according to the present invention, reacting Compound I and Compound II is performed in an organic solvent.

Representative examples of organic solvents that suitable for use in the process according to the present invention include, without limitation, one or more of methanol, ethanol, 1-propanol, 2-propanol, 1-butanol, 2-butanol and any combinations thereof.

As is further demonstrated in the Examples section that follows, exceptional results have been obtained using 1-propanol as the reaction solvent.

As is further demonstrated in the Examples section that follows, and in accordance with the findings and rationale set forth above, even more exceptional results were obtained when the process was performed in a mixture of an organic solvent (e.g., 1-propanol) and water.

Thus, according to a preferred embodiment of the present invention, the reaction solvent comprises water and 1-propanol. Preferably, the ratio between 1-propanol to water ranges from about 20:1 to about 1:1. More preferably, the ratio of 1-propanol to water is about 18:1.

The above ratios between an organic solvent and water are expected to produce similar results when using any of the aforementioned organic solvents.

The relative amounts of the starting materials in this process, namely, 6-hydroxy-3,4-dihydroquinolin-2(1H)one (Compound I) and 5-(4-chlorobutyl)-1-cyclohexyl-1H-tetrazole(Compound II), are preferably selected so as to achieve the optimal chemical yield and purity of the product. According to a preferred embodiment of the present invention, the relative amounts of Compound I and Compound II are selected such that the molar ratio therebetween ranges from about 1:1 to about 2:1. More preferably, the molar ratio between Compound I and Compound II is about 1.3:1.

Reacting Compound I and Compound II in the presence of a hydrated inorganic base can be performed at any selected temperature which does not lead to decomposition of one or more of the reactants or the product. Preferably, the reaction is performed in the presence of a solvent, as described hereinabove, and the reaction temperature ranges between room temperature and the reflux temperature of the solvent. More preferably, the reaction is performed at the reflux temperature of the solvent.

The reaction time evidently depends on the temperature at which the reaction is performed and hence may range, for example, from about 5 hours to about 15 hours. When the reaction is performed at the reflux temperature of 1-propanol, with or without water, the reaction time is typically 7-8 hours.

Using the conditions described hereinabove, the above reaction, when completed, results in a reaction mixture that comprises cilostazol.

As is demonstrated in the Examples section that follows, the thus obtained cilostazol can be readily isolated from the reaction mixture by cooling the mixture to a temperature lower than 15° C., preferably to a temperature of about 10-15° C., so as to allow the precipitation of the cilostazol. The precipitated cilostazol can thereafter be isolated from the reaction mixture by conventional methods such as filtration.

As is further demonstrated in the Examples section that follows, the cilostazol is obtained by this process in a relatively high yield. More specifically, the cilostazol yield is greater than 75%, more preferably, greater then 79% and in some cases, is about 85%.

The thus obtained cilostazol has a purity, as determined by HPLC, greater than 99.5%. As is shown by the HPLC measurements conducted (see Examples section that follows for a detailed HPLC protocol), the cilostazol contained no more than 0.23% of the impurity Compound III and, in some experiments, no more than 0.12%. The cilostazol further contained residual amounts of the starting material Compound I.

The thus obtained Cilostazol can be readily purified so as to remove residual amounts of the starting materials and traces of Compound III. Hence, according to a preferred embodiment of the process according to the present invention, the process further comprises purifying the isolated crude cilostazol. The purifying of the cilostazol is preferably effected by simple batch purification methods such as slurrying and/or recrystallization.

Thus, according to a preferred embodiment of the present invention purifying the cilostazol is effected by slurrying the cilostazol in an organic solvent.

In a typical procedure, the slurrying is effected by:

mixing the isolated cilostazol in an organic solvent;

heating the slurry to reflux temperature of the organic solvent;

cooling the slurry to room temperature; and collecting the cilostazol by filtration.

Suitable organic solvents for use in this context of the present invention include solvents in which the cilostazol is readily dissolvable whereby the impurities Compound III and/or Compound I are hardly dissolvable. A preferred organic solvent for use in the slurrying procedure is ethyl acetate.

According to another preferred embodiment of the present invention, purifying the cilostazol is effected by recrystallizing the isolated cilostazol. Preferably, the recrystallization procedure is effected in a mixture of an organic solvent and an aqueous solution of an inorganic base.

In a typical procedure, recrystallizing the cilostazol is effected by;

dissolving the isolated crude cilostazol in an organic solvent;

heating the solution to reflux temperature of the organic solvent;

adding to the solution an aqueous solution of an inorganic base and water;

filtering the hot mixture;

cooling the solution to a temperature lower than 15° C.; and collecting the thus precipitated cilostazol by filtration.

Suitable organic solvents for use in this context of the present invention include, without limitation, lower alcohols such as 1-propanol, methanol, ethanol, 1-butanol and 2-butanol, preferably 1-propanol.

Suitable aqueous solutions of an inorganic base for use in this context of the present invention include, without limitation, aqueous solutions of alkali metal hydroxides such as sodium hydroxide and potassium hydroxide, preferably sodium hydroxide. The concentration of the inorganic base in the aqueous solution is selected sufficient to bring the pH of the solution to about 11. An exemplary preferred aqueous solution of an inorganic base is a 47% aqueous solution of sodium hydroxide.

According to a preferred embodiment of the present invention, purifying the cilostazol is effected by slurrying and recrystallizing the isolated cilostazol, as described hereinabove, whereby either the slurrying procedure precedes the recrystallizing procedure or the recrystallizing procedure precedes the slurrying procedure.

As is demonstrated in the Examples section that follows, upon the purification of the isolated cilostazol, highly pure cilostazol is obtained.

Particularly, the thus obtained cilostazol has a purity of at least 99.9% and, is some cases, of at least 99.95%, as determined by HPLC measurements. The thus obtained cilostazol contains no more than 0.1 weight percent of Compound III and in most cases is free of any detectable amounts of Compound III.

The process of the present invention is therefore highly advantageous as compared with the processes known and used hitherto since it obviates the use of hazardous, expensive and environmentally unfriendly reagents while further providing a highly pure cilostazol which is substantially free of the impurity Compound III.

Figure 4:
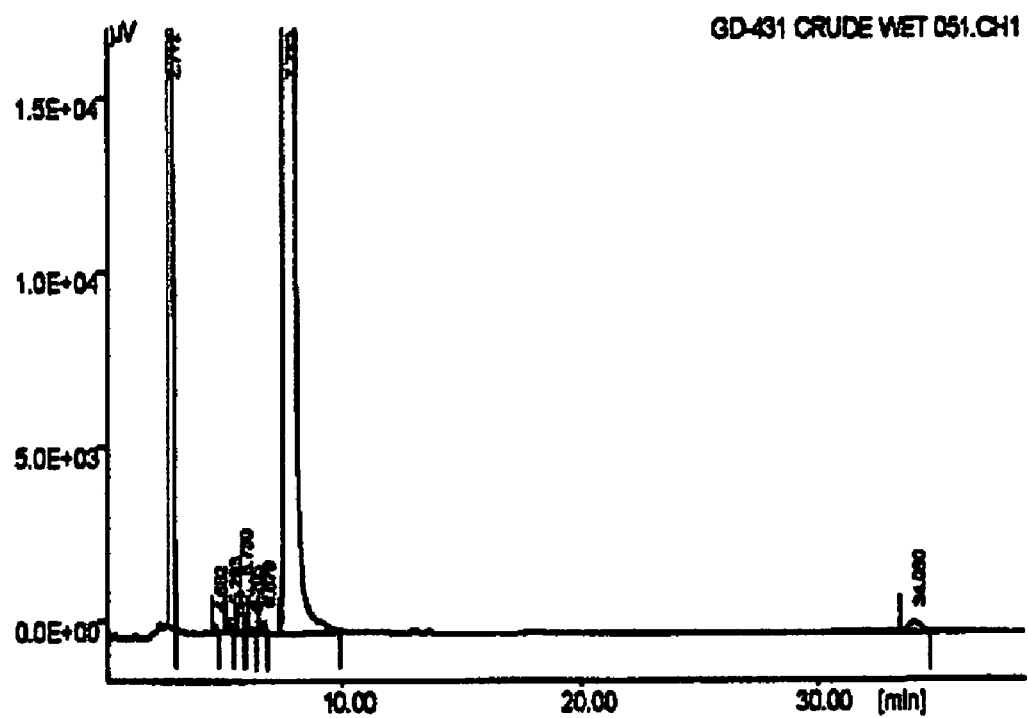
FIG. 4 presents an HPLC chromatogram of the crude cilostazol obtained by an exemplary process according to preferred embodiments of the present invention (see, Example 3 hereinunder), which indicates that the crude product contains 2.705% of Compound I (retention time 2.712 minutes, area=267027.998), 0.012%, 0.035%, 0.121, 0.015 and 0.032% of unidentified impurities (having retention times at 4.682, 5.293, 5.730, 6.205 and 6.678 minutes, respectively), 96.985% of cilostazol (retention time 7.732 minutes, area=9573491.271) and 0.095% of Compound III (retention time 34.080 minutes, area=9340.153), whereby the total peak area is 9871138.149 [µV.sec]
Figure 5:
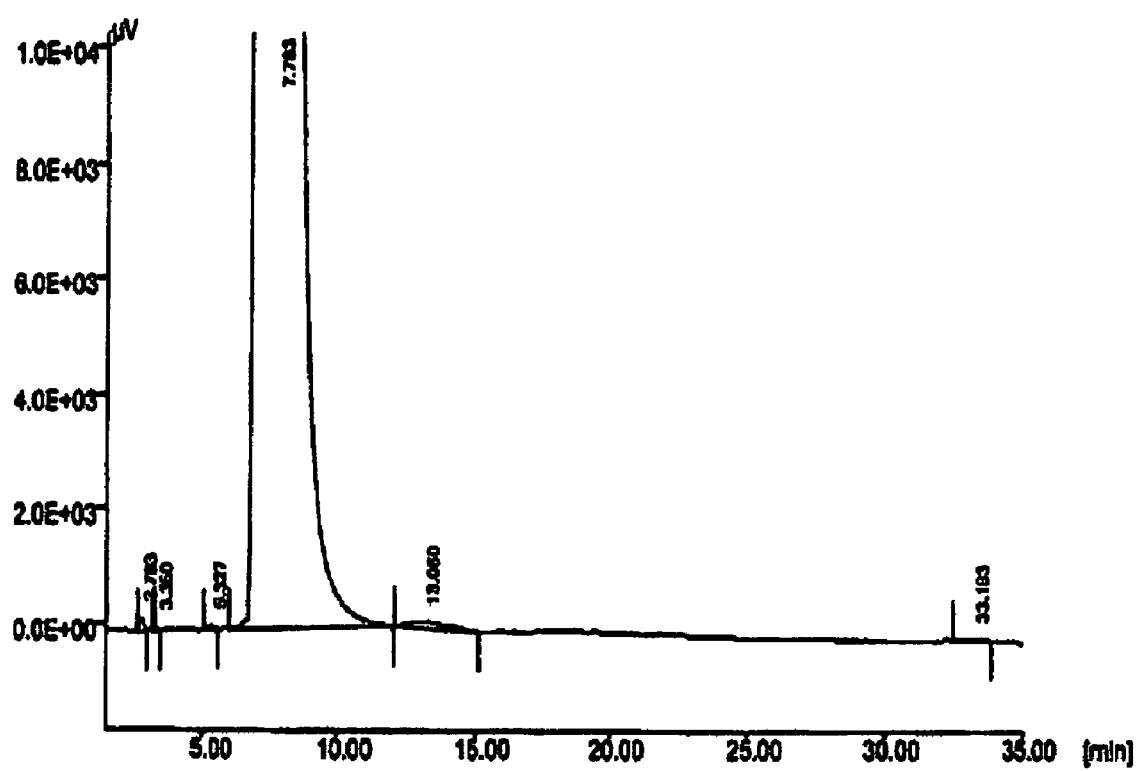
FIG. 5 presents an HPLC chromatogram of a purified cilostazol obtained by an exemplary process according to preferred embodiments of the present invention (see, Example 3 hereinunder), which indicates that the purified product contains 0.007% of Compound I (retention time 2.783 minutes, area=1635.288), 0.002% and 0.004% of unidentified impurities (having retention times at 3.350 and 5.327 minutes, respectively), 99.935% of cilostazol (retention time 7.763 minutes, area=23885092.009), 0.044% of an impurity (retention time 13.060 minutes) and 0.008% of Compound III (retention time 33.183 minutes, area=1970.450), whereby the total peak area is 23900578.260 [µV.sec].

HPLC chromatograms of a crude and a purified cilostazol obtained by an exemplary process according to the present invention (see, Example 3 in the Examples section that follows) are presented in FIGS. 4 and 5 respectively, and clearly show that only minute amount of Compound III was obtained in the crude product while no detectable traces of this impurity were obtained in the purified cilostazol. Comparing these results with those obtained while reproducing the prior art processes (see, Reference Examples 1-7 and FIGS. 1-3) clearly demonstrate the superiority of the process according to the present invention.

Thus, according to another aspect of the present invention, there is provided cilostazol which is substantially free of the impurity N-[4-(1-cyclohexyl-1H-tetrazol-5-yl)butyl]-6-[4-(1-cyclohexyl-1H-tetrazol-5-yl) butoxy]-3,4-dihydro-2(1H)-quinolinone (Compound III).

As used herein, the phrase "substantially free of" refers to a compound, herein, cilostazol, which includes a negligible amount of another compound, herein Compound III, and, more particularly, which includes no more than 0.1 weight percent of another compound.

Preferably, the content of Compound III is less than 0.1 weight percent, more preferably it is less than 0.06 weight percent, and even more preferably no detectable amounts of Compound III are present in the cilostazol.

Thus, the cilostazol, according to this aspect of the present invention, has a purity of at least 99.5 weight percents, more preferably a purity that equals to or is higher than 99.9 weight percents and even more preferably, a purity that equals to or is higher than 99.95 weight percents.

Using the process described herein, and the general features thereof as detailed hereinabove, derivatives and analogs of cilostazol can also be readily prepared in high purity and yield.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

General Protocol for HPLC Analyses:

HPLC analyses were carried out using a reverse phase Luna C8(2), 5 μ, 250×4.6 mm Phenomenex column (P/N 00G-4249-EO from Ophir Analytical), using a 53% phosphate buffer (6.8 grams of potassium dihydrogen phosphate in 1 liter of water, with pH adjusted with phosphoric acid to 4.0): 47% acetonitrile mobile phase.

Flow rate was set to 1.0 ml per minute.

Sample injection volume was offset to 20 μl.

Peak detection was accomplished with a UV detector operated at 254 nm.

The overall runtime was 40 minutes.

Preparation of Stock Solutions and Standard Solutions for Quantitative Analyses:

A stock solution of 6-hydroxy-3,4-dihydroquinolin-2(1H)-one (Compound I) was prepared as follows:

25 mg of Compound I were weighed accurately and placed in a 25.0 ml volumetric flask, were dissolved in a solution of the mobile phase described above, and the flask volume was completed with the solution of the mobile phase.

A stock solution of 6-[4-(1-cyclohexyl-1H-tetrazol-5-yl)-butoxy]-1-[4-(1-cyclohexyl-1H-tetrazol-5-yl)-butyl]-3,4-dihydro-1H-quinolin-2-one (Compound III) was prepared as follows:

25 mg of Compound III were weighed accurately and placed in a 25.0 ml volumetric flask, were dissolved in acetonitrile, and the flask volume was completed with acetonitrile.

A standard solution of Compound I and Compound III (herein, Solution A) was prepared as follows:

1.0 ml of each of the above stock solutions of Compounds I and III were transferred to a 10.0 ml volumetric flask and the flask volume was completed with the solution of the mobile phase.

A standard solution of cilostazol, Compound I and Compound III was prepared as follows:

100 mg of cilostazol were weighed accurately and placed in a 50.0 ml volumetric flask. 1.0 ml of Solution A was added, cilostazol was dissolved and the flask volume was completed with the solution of the mobile phase.

A diluted stock solution of cilostazol was prepared as follows:

25 mg of cilostazol were weighed accurately and placed in a 25.0 ml volumetric flask, dissolved in the solution of the mobile phase, and the volume was completed with the solution of the mobile phase.

1.0 ml of the obtained solution was transferred to a 10.0 ml volumetric flask and the flask volume was completed with the solution of the mobile phase, thus obtaining Solution B.

1.0 ml of Solution B was transferred to a 50.0 ml volumetric flask, and the flask volume was completed with the solution of the mobile phase, thus obtaining a 0.1% solution of cilostazol.

A diluted standard solution of Compound I and Compound III was prepared as follows:

1.0 ml of Solution A was transferred to a 50.0 ml volumetric flask, and the volume complete to with the solution of the mobile phase, thus obtaining a 0.1% solution of both Compounds I and III.

Preparation of Tested Sample Solutions for HPLC Analysis:

100.0 mg of each of the samples to be analyzed were weighed accurately and placed in a 50.0 ml volumetric flask, dissolved in the solution of the mobile phase and the volume was complete the solution of the mobile phase.

Validated Retention Time for Cilostazol, Compound I and Compound III:

Using the above analyses conditions, the following retention times were observed:

Compound I: about 2.9 minutes;

Cilostazol: about 7.5 minutes; and

Compound III: about 31 minutes.

Evaluation of the Weight Percent Contents of Compound I and Compound III:

The HPLC peaks of Compounds I and III were identified by their validated retention times. The relative content of each compound was calculated using the following formula:

$$\% \text{ content} = \frac{W_{std} \times A_{\text{sample}}}{A_{std} \times W_{\text{sample}}} \times 100$$

wherein:

$A_{sample}$ is the peak area of Compound I or Compound III in the tested sample solution;

$A_{std}$ is the peak area of Compound I or Compound III in the standard solution of Compounds I and III;

$W_{std}$ is the actual measured weight in mg of Compound I or Compound III in the standard solution of Compounds I and III;

$W_{sample}$ is the actual measured weight in mg of the tested sample in the tested sample solution.

Reference Example 1

U.S. Pat. No. 4,277,479 (Examples 4 and 26)

The preparation of Cilostazol in the presence of 1,8-diazabicyclo[5,4,0]undec-7-ene (DBU) was carried out according to Examples 4 and 26 of U.S. Pat. No. 4,277,479.

3.22 grams of 6-hydroxy-3,4-dihydroquinolin-2(1H)one (Compound I, 0.0195 mole) and 3.51 ml of DBU (0.0230 mole) were mixed in 100 ml of ethanol, and the mixture was heated to reflux. A solution of 5.17 grams of 5-(4-chlorobutyl)-1-cyclohexyl-1H-tetrazole (Compound II, 0.0211 mole), in 100 ml ethanol was added dropwise over a time period of 90 minutes to the mixture containing Compound I and DBU. The reaction mixture was heated to reflux for 5 additional hours and concentrated thereafter by evaporation under vacuum. Fifty ml of water were added to the concentrated residue, and the mixture was stirred for 3 hours. The formed precipitate was collected by filtration, washed with water and dried at 50° C. overnight to afford 4.78 grams of crude product at 61.3% yield.

HPLC analysis of the crude product, performed according to the protocol described hereinabove, showed a composition of 98.63% of the desired Cilostazol, 0.33% of Compound I and 0.31% of the impurity 6-[4-(1-cyclohexyl-1H-tetrazol-5-yl)-butoxy]-1-[4-(1-cyclohexyl-1H-tetrazol-5-yl)-butyl]-3,4-dihydro-1H-quinolin-2-one (Compound III).

The 4.78 grams of the crude product were further purified by recrystallization from a mixture of 15 ml of ethanol and 2 ml of water to afford 3.14 grams of crystalline Cilostazol at an overall yield of 40.2%.

The HPLC analysis, performed as described above, of the purified product showed a composition of 99.72% of the desired Cilostazol, 0.08% of Compound I and 0.1% of the impurity Compound III.

Reference Example 2

(Nishi et al.)

The preparation of Cilostazol in the presence of potassium hydroxide in 2-propanol was carried out according to Nishi, T. et al., *Chem. Pharm. Bull.*, 1983, 31, pp. 1151-57.

16.3 grams of 6-hydroxy-3,4-dihydroquinolin-2(1H)-one (Compound I, 0.98 mole) and 7 grams of flaked potassium hydroxide (0.112 mole) were mixed in 100 ml of 2-propanol, and the mixture was heated to reflux A solution of 28.5 grams of 5-(4-chlorobutyl)-1-cyclohexyl-1H-tetrazole (Compound II, 0.116 mole), in 75 ml 2-propanol was added dropwise over a time period of 45 minutes. to the mixture containing Compound I and potassium hydroxide. The reaction mixture was heated to reflux for 5 additional hours and concentrated thereafter by evaporation under vacuum. The concentrated residue was extracted with chloroform, and the extract was washed successively with 1N NaOH, diluted HCl and water, and dried thereafter over $Na_2SO_4$. The chloroform was removed under vacuum, and the residue was dried at 50° C. overnight to afford 35.9 grams of crude product at 83% yield.

HPLC analysis, performed as described above, of the crude product showed a composition of 87.60% of the desired Cilostazol, 6.42% of Compound I, and 5.75% of the impurity Compound III.

The 35.9 grams of the crude product were further purified by recrystallization from 555 ml of methanol to afford 24.5 grams of Cilostazol at an overall yield of 57.2%.

HPLC analysis, performed as described above, of the purified product showed a composition of 98.33% of the desired Cilostazol and 1.64% of the impurity Compound III.

Reference Example 3

U.S. Pat. Nos. 6,515,128(Example 1) and 6,825,214 (Example 1)

The preparation of Cilostazol using a phase transfer catalyst was carried out according to Example 1 in both U.S. Pat. Nos. 6,515,128 and 6,825,214.

A mixture of 22.22 grams of 5-(4-chlorobutyl)-1-cyclohexyl-1H-tetrazole (Compound II, 0.0915 mole), 17 grams of $Na_2SO_4$ and 1.9 grams of the catalyst Aliquate®336, stirred in 15 ml toluene, was added to a 90 ml aqueous solution containing 16.5 grams of 6-hydroxy-3,4-dihydroquinolin-2(1H)-one (Compound I, 0.1011 mole) and one equivalent of NaOH. The mixture was heated to reflux for 8 hours, and cooled thereafter to room temperature. The solid precipitant was filtered, washed with water and methanol to afford 29 grams of crude product at 85.8% yield.

HPLC analysis, performed as described above, of the crude product showed a composition of 99.49% of the desired Cilostazol and 0.25% of the impurity Compound III.

The 29 grams of the crude product were further purified by recrystallization from 380 ml of methanol to afford 26.4 grams of crystalline Cilostazol at an overall yield of 78.1%.

HPLC analysis, performed as described above, of the purified product showed a composition of 99.76% of the desired Cilostazol and 0.12% of the impurity Compound III.

Reference Example 4

U.S. Pat. Nos. 6,515,128 (Example 2) and 6,825,214 (Example 2)

The preparation of Cilostazol with addition of 5-(4-chlorobutyl)-1-cyclohexyl-1H-tetrazole in one portion was carried out according to Example 2 in U.S. Pat. Nos. 6,515,128 and 6,825,214.

A mixture of 18 grams of 5-(4-chlorobutyl)-1-cyclohexyl-1H-tetrazole (Compound II, 0.0742 mole), 10 grams of 6-hydroxy-3,4dihydroquinolin-2(1H)-one (Compound I, 0.0613 mole), 4.05 grams of flaked potassium hydroxide (0.0650 mole) and 1.5 grams of $K_2CO_3$ (0.011 mole) was stirred in 130 ml of 1-butanol, heated to reflux for 5 hours, and cooled thereafter to room temperature. The solid precipitants was filtered, washed with 1-butanol and water and dried overnight at 50° C. to afford 19.1 grams of crude product at 69.7% yield.

HPLC analysis, performed as described above, of the crude product showed a composition of about 97% of the desired Cilostazol, 0.92% of Compound I and 1.68 % of the impurity Compound III. The corresponding HPLC chromatogram is presented in FIG. 1 and clearly shows the presence of a significant amount of the impurity Compound III, at a retention time of 31.5 minutes.

The crude product was further purified by recrystallization from 190 ml of 1-butanol to afford 17.95 grams of crystalline Cilostazol at an overall yield of 65.5%.

HPLC analysis, performed as described above, of the recrystallized product showed a composition of 99.23% of the desired Cilostazol and 0.52% of the impurity Compound III. The corresponding HPLC chromatogram is presented in FIG. 2 and clearly shows that a significant amount of the impurity Compound III is still detected at a retention time of 34 minutes.

The 17.95 grams of the recrystallized Cilostazol were re-recrystallized again from 360 ml of 1-butanol to afford 16 grams of doubly purified crystalline Cilostazol at an overall yield of 58.4%.

HPLC analysis, performed as described above, of the purified product showed a composition of 99.33% of the desired Cilostazol and 0.41% of the impurity Compound III. FIG. 3 presents the corresponding HPLC chromatogram and clearly shows that no significant reduction of the amount of the impurity Compound III was obtained by the consecutive recrystallization steps.

Reference Example 5

U.S. Pat. Nos. 6,515,128 (Example 3) and 6,825,214 (Example 3)

The preparation of Cilostazol with addition of potassium hydroxide in several portions was carried out according to Example 3 in U.S. Pat. Nos. 6,515,128 and 6,825,214.

A mixture of 10 grams of 6-hydroxy-3,4-dihydroquinolin-2(1H)-one (Compound I, 0.0613 mole), 13.4 grams of 5-(4-chlorobutyl)-1-cyclohexyl-1H-tetrazole (Compound II, 0.0552 mole), 1.01 grams of flaked potassium hydroxide (0.0162mole) and 1.5 grams of $K_2CO_3$ (0.011 mole), was stirred in 130 ml of 1-botanol and heated to reflux for one hour. Thereafter, a second portion of 1.1 grams of flaked potassium hydroxide was added to the reaction mixture, and the reflux was allowed to continue for an additional 1 hour. The routine of addition of 1.1 grams of potassium hydroxide was repeated twice more, each time allowing the reaction mixture to reflux for an additional hour. The reaction mixture was then cooled to room temperature, and the solid was collected by filtration, washed with 1-butanol and dried at 50° C. overnight to afford 11.4 grams of crude product at 55.9% yield.

HPLC analysis, performed as described above, of the crude product showed a composition of 93.50% of the desired Cilostazol, 5.6% of Compound I and 0.27% of the impurity Compound III.

Reference Example 6

U.S. Pat. Nos. 6,515,128 (Example 4) and 6,825,214 (Example 4)

The preparation of Cilostazol using molecular sieves as a dehydrating agent was carried out according to Example 4 in U.S. Pat. Nos. 6,515,128 and 6,825,214.

A mixture of 10 grams of 6-hydroxy-3,4dihydroquinolin-2(1H)-one (Compound I, 0.0613 mole), 4.05 grams of flaked potassium hydroxide (0.0650 mole) and 1.5 grams of $K_2CO_3$ (0.011 mole), was stirred in 130 ml of 1-botanol in a flask equipped with a soxhlet extraction apparatus containing 28 grams of 3 Å molecular sieves. The mixture was heated to reflux while passing the solvent over the molecular sieves for 30 minutes. Thereafter 18 grams of 5-(4-chlorobutyl)-1-cyclohexyl-1H-tetrazole (Compound II, 0.0742 moles, which are 1.2 equivalents with respect to Compound I) were added and the reflux was allowed to continue for about 5 hours. The reaction mixture was cooled thereafter to room temperature, and the solid product was collected by filtration, washed with 1-butanol and water and dried at 50° C. overnight to afford 19.2 grams of crude Cilostazol at 70.0% yield.

HPLC analysis, performed as described above, of the crude product showed a composition of 98.46% of the desired Cilostazol, 0.26% of Compound I and 0.68% of the impurity Compound III.

Reference Example 7

U.S. Pat. Nos. 6,515,128 (Example 5) and 6,825,2.14 (Example 5)

The preparation of Cilostazol using excess of 6-hydroxy-3,4-dihydroquinolin-2(1H)-one was carried out according to Example 5 in U.S. Pat. Nos. 6,515,128 and 6,825,214.

A mixture of 13.4 grams of 5-(4-chlorobutyl)-1-cyclohexyl-1H-tetrazole (Compound II, 0.0552 mole), 10 grams of 6-hydroxy-3,4-dihydroquinolin-2(1H)-one (Compound I, 0.0613 mole), 4.05 grams of flaked potassium hydroxide (0.0650 mole) and 1.5 grams of $K_2CO_3$ (0.011 mole) was stirred in 130 ml of 1-butanol, heated to reflux for 5 hours, and cooled thereafter to room temperature. The solid precipitant was filtered, washed with 1-butanol and water and dried overnight at 50° C. to afford 16.1 grams of crude product at 79.0% yield.

HPLC analysis, performed as described above, of the crude product showed a composition of 96.87% of the desired Cilostazol, 1.2% of Compound I and 1.6% of the impurity Compound III.

The 16.1grams of the crude product were further purified by recrystallization from 210 ml of methanol to afford 13.3 grams of crystalline Cilostazol at an overall yield of 65.2%.

HPLC analysis, performed as described above, of the purified product showed a composition of 99.5% of the desired Cilostazol and 0.35% of the impurity Compound III.

Example 1

48.6 grams of 5-(4-chlorobutyl)-1-cyclohexyl-1H-tetrazole (Compound II, 0.2 mole), 42.2 grams of 6-hydroxy-3,4-dihydroquinolin-2(1H)-one (Compound I, 0.259 moles, 1.3 mol equivalents with respect to Compound II) and 16.1 grams of 85% potassium hydroxide powder (0.245 mole, 1.22 mol equivalents with respect to Compound II) were added to 1-propanol (450 ml). The resulting mixture was heated under reflux for 7 hours. The hot reaction mixture was then filtered and the filtrate was cooled to 10-15° C. during 6 hours. The solid precipitate was collected thereafter by filtration, washed with 1-propanol (50 ml), water (two portions of 50 ml), and again with 1-propanol (50 ml), and dried at 50° C. overnight. 59 grams (79.8% yield) of a crude product were thus obtained.

HPLC analysis, performed as described above, of the crude product showed a composition of 99.03% of the desired Cilostazol, 0.48% of Compound I and 0.28% of the impurity Compound III.

The crude product (59 grams) was slurried in ethyl acetate (180 ml) and the resulting slurry was heated under reflux for 3 hours. Thereafter, the mixture was cooled to room temperature, and the solid precipitate was collected by filtration, washed with ethyl acetate (100 ml) and dried at 50° C. for 5 hours. 55 grams (74.4%. yield) of the product were thus obtained.

HPLC analysis, performed as described above, of the obtained product showed a composition of 99.55% of the desired Cilostazol, 0.23% of Compound I and 0.14% of the impurity Compound III.

The product obtained above (55 grams) was dissolved in 1-propanol (390 ml) and the resulting solution was heated under reflux. A 47% aqueous solution of NaOH (about 1.5 grams) and water (20 ml) were added thereafter to reach an alkaline pH of about 11. The hot solution was filtered, and the filtrate was cooled to 10-15° C. during 6 hours. The precipitate, in the form of crystals, was collected thereafter by filtration, washed with water (two portions of 75 ml) and 1-propanol (75 ml) and dried at 50° C. overnight 52 grams of pure Cilostazol (70.4% yield) were thus obtained.

HPLC analysis, performed as described above, of the final product showed a composition of 99.88% of the desired Cilostazol and 0.06% of the impurity Compound III.

Example 2

48.6 grams of 5-(4-chlorobutyl)-1-cyclohexyl-1H-tetrazole (Compound II, 0.2 mole), 42.2 grams of 6-hydroxy-3,4-dihydroquinolin-2(1H)-one (Compound I, 0.259 moles, 1.3 mol equivalents with respect to Compound II) and 16.1 grams of 85% potassium hydroxide powder (0.245 mole, 1.22 mol equivalents with respect to Compound II) were added to 1-propanol (450 ml). The resulting mixture was heated under reflux for 7 hours. Thereafter, water (100 ml) was added to the reaction mixture, and heating under reflux was continued until the contents were dissolved. The solution of the reaction mixture was cooled to 10-15° C. during 6 hours. The solid precipitate was collected thereafter by filtration, washed with 1-propanol (50 ml), water (two portions of 50 ml), and again with 1-propanol (50 ml), and dried at 50° C. overnight. 58.7 grams (79.4% yield) of a crude product were thus obtained.

HPLC analysis, performed as described above, of the crude product showed a composition of 99.04% of the desired Cilostazol, 0.54% of Compound I and 0.23% of the impurity Compound III.

The crude product (58.7 grams) was dissolved in 1-propanol (410 ml) and the resulting solution was heated under reflux. A 47% aqueous solution of NaOH (about 1.5 grams) and water (20 ml) were added thereafter to reach alkaline conditions of about pH 11. The hot solution was filtered, and the filtrate was cooled to 10-15° C. during 6 hours. The precipitate, in the form of crystals, was thereafter collected by filtration, washed with water (two portions of 75 ml) and 1-propanol (75ml), and dried at 50° C. overnight. 55 grams of recrystallized Cilostazol (74.4% yield) were thus obtained.

HPLC analysis, performed as described above, of the recrystallized product showed a composition of 99.84% of the desired Cilostazol and 0.11% of the impurity Compound III.

The recrystallized product obtained above (55 grams) was slurried in ethyl acetate (165 ml) and the resulting slurry was heated under reflux for 3 hours. Thereafter the mixture was cooled to room temperature, and the precipitated solid was collected by filtration, washed with ethyl acetate (50 ml) and dried at 50° C. overnight. 51.9 grams (70.2% yield) of purified Cilostazol were thus obtained.

HPLC analysis, performed as described above, of the purified product showed a composition of 99.96% of the desired Cilostazol. No other impurities were identified.

Example 3

24.3 grams of 5-(4-chlorobutyl)-1-cyclohexyl-1H-tetrazole (Compound II, 0.1 mole), 21.1 grams of 6-hydroxy-3,4-dihydroquinolin-2(1H)-one (Compound I, 0.13 moles, 1.3 mol equivalents with respect to Compound II) and 8 grams of 85% flaked potassium hydroxide (0.122 mole, 1.22 equivalents with respect to Compound II) were added to 1-propanol (225 ml) and water (12.5 ml). The resulting mixture was heated under reflux for 8 hours and then cooled to 10-15° C. during 6 hours. The solid precipitate was collected thereafter by filtration, washed with 1-propanol (25 ml), water (two portions of 25 ml), and again with 1-propanol (25 ml), and dried at 50° C. overnight. 31.4 grams (85% yield) of a crude product were thus obtained.

HPLC analysis, performed as described above, of the crude product showed a composition of 99.14% of the desired Cilostazol, 0.63% of Compound I and 0.20% of the impurity Compound III. The corresponding HPLC chromatogram is presented in FIG. 4. Comparing FIG. 4 to FIGS. 1-3 clearly show the substantially reduced amount of the impurity Compound III obtained by this exemplary process of the present invention as compared with the amount of the same impurity even after two consecutive recrystallizations of the product obtained by the prior art process.

The crude product (31.4 grams) was dissolved in 1-propanol (220 ml) and the resulting solution was heated under reflux. A 47% aqueous solution of NaOH (about 0.8 grams) and water (10 ml) were added thereafter to reach alkaline pH of about 11. The hot solution was filtered, and filtrate was cooled to 10-15° C. during 6 hours. The formed crystals were collected by filtration, washed with water (two portions of 30 ml) and 1-propanol (40 ml), and dried at 50° C. overnight. 28.8 grams (78% yield) of recrystallized Cilostazol were thus obtained.

HPLC analysis, performed as described above, of the recrystallized Cilostazol showed a composition of 99.63% of the desired Cilostazol and 0.12% of the impurity Compound III.

The recrystallized Cilostazol (22.8 grams) was slurried in ethyl acetate (70 ml) and the resulting slurry was heated under reflux for 3 hours. Thereafter the mixture was cooled to room temperature, and the precipitated solid was collected by filtration, washed with ethyl acetate (25 ml) and dried overnight at 50° C. 28.4 grams (76.8% yield) of pure Cilostazol were thus obtained.

HPLC analysis, performed as described above, of the purified product showed a composition of 99.90% of the desired Cilostazol. No other impurities were identified. The corresponding HPLC chromatogram is presented in FIG. 5 and clearly show that no traces of the impurity Compound III were detected.

Example 4

The preparation of 6-(4(1-cyclohexyl-1H-tetrazol-5-yl) butoxy)-1-(4-(1-cyclohexyl-1H-tetrazol-5-yl) butyl)-3,4-dihydroquinolin-2(1H)-one (Compound III) was carried out by adding 20 grams of Cilostazol (0.0541 mole, obtained as described in Examples hereinabove) to anhydrous N,N-dimethylformamide (200 ml) under dry nitrogen. The resulting mixture was cooled to 10-15° C., and 2.81 grams of 60% NaH powder in oil (0.0703 mole, 1.3 mol equivalents with respect to Cilostazol) were then added in two portions over a time period of 1.5 hours, while maintaining a temperature of 10-15° C. The mixture was stirred for additional 2 hours at 10-15° C., and 15.75 grams of 5-(4-chlorobutyl)-1-cyclohexyl-1H-tetrazole (Compound II, 0.0649 mole, 1.2 mol equivalents with respect to Cilostazol), were added. The reaction mixture was stirred at room temperature for 24 hours. Water (600 ml) was added thereafter to the reaction mixture, and the mixture was stirred for one hour. The aqueous layer was removed by decantation from the syrup-like organic layer. The organic layer was stirred with water (300 ml) for half an hour at room temperature, and the aqueous layer was removed again by decantation. Methanol (50 ml) was added to the syrup-like organic layer after decantation of the water, and the resulting mixture was heated to obtain a homogeneous solution. The solution was cooled to 10-15° C. during 3 hours and the methanol was removed by decantation. The addition of methanol, followed by heating, cooling and decantation of the methanol was repeated three times. The syrup-like organic layer was thereafter slurried in diethyl ether and in n-hexane at room temperature, and was then dried at 50° C. overnight. 15 grams of 6-(4-(1-cyclohexyl-1H-tetrazol-5-yl)butoxy)-1-(4-(1-cyclohexyl-1H-tetrazol-5-yl) butyl)-3,4-dihydroquinolin-2(1H)-one (Compound III) were thus obtained as a monosolvate in methanol.

HPLC analysis, performed as described above, indicated that Compound III was obtained at a purity of 98%.

Calculated elemental analysis for $C_{31}H_{45}N_9O_2$—$CH_3OH$ (607.79) anticipated: 63.17% C; 8.12% H; 20.73% N. Measured elemental analysis found: 62.82% C; 7.96% H; 20.82% N.

Mass spectroscopy using the fast-atom bombardment method showed mass-over-charge peak (m/z) at 576.3 ($MH^+$).

It is appreciated that certain features of the invention, which are, for clarity, described in the context of separate embodiments, may also he provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the arts Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A process of preparing 6-(4-(1-cyclohexyl-1H-tetrazol-5-yl)butoxy)-3,4-dihydro-2(1H)-quinolinone (Cilostazol), the process comprising:
    reacting 6-hydroxy-3,4-dihydroquinolin-2(1H)-one with 5-(4-chlorobutyl)-1-cyclohexyl-1H-tetrazole in the presence of a hydrated inorganic base, to thereby obtain a reaction mixture containing Cilostazol;
    isolating the Cilostazol from the reaction mixture;
    slurrying the Cilostazol in an organic solvent; and
    crystallizing the Cilostazol in the presence of a base, to produce Cilostazol, which is substantially free of N-[4-(1-cyclohexyl-1H-tetrazol-5-yl)butyl]-6-[4-(1-cyclohexyl-1H-tetrazol-5-yl)butoxy]-3,4-dihydro-2(1H)-quinolinone, and has a purity of at least 99.9%.

2. The process of claim 1, wherein the cilostazol contains less than 0.06 weight percent N-[4-(1-cyclohexyl-1H-tetrazol-5-yl)butyl]-6-[4-(1-cyclohexyl-1H-tetrazol-5-yl)butoxy]-3,4-dihydro-2(1H)-quinolinone.

3. The process of claim 1, wherein said hydrated inorganic base contains at least 5 weight percentages of water.

4. The process of claim 1, wherein said hydrated inorganic base contains at least 10 weight percentages of water.

5. The process of claim 1, wherein said hydrated inorganic base contains at least 15 weight percentages of water.

6. The process of claim 1, wherein said reacting is performed in a solvent.

7. The process of claim 6, wherein said solvent comprises methanol, ethanol, 1-propanol, 2propanol, 1-butanol, 2-butanol or a combination thereof.

8. The process of claim 7, wherein said solvent further comprises water.

9. The process of claim 8, wherein said solvent comprises a mixture of 1-propanol and water.

10. The process of claim 9, wherein the ratio between said 1-propanol and said water ranges from 20:1 to 1:1.

11. The process of claim 10, wherein said ratio is 18:1.

12. The process of claim 1, wherein said inorganic base is sodium hydroxide, potassium hydroxide, sodium carbonate, potassium carbonate, sodium bicarbonate or potassium bicarbonate.

13. The process of claim 1, wherein said inorganic base is potassium hydroxide.

14. The process of claim 1, wherein the molar ratio between said 6-hydroxy-3,4-dihydroquinolin-2(1H)-one and said 5-(4-chlorobutyl)-1-cyclohexyl-1H-tetrazole ranges from about 1:1 to about 2:1.

15. The process of claim 14, wherein said molar ratio is about 1.3:1.

16. The process of claim 1, wherein the molar ratio between said hydrated inorganic base and said 5-(4-chlorobutyl)-1-cyclohexyl-1H-tetrazole ranges from about 1:1 to about 2:1.

17. The process of claim 16, wherein said molar ratio is about 1.2:1.

18. The process of claim 6, wherein said reacting is performed at the reflux temperature of said solvent.

19. The process of claim 1, wherein said isolating is effected by precipitating the cilostazol from said reaction mixture at a temperature lower than 15° C.

20. The process of claim 1, wherein said slurrying precedes said crystallizing.

21. The process of claim 1, wherein said crystallizing precedes said slurrying.

22. The process of claim 1, wherein said slurrying is performed in ethyl acetate.

23. The process of claim 1, wherein said crystallizing is performed in 1-propanol.

24. The process of claim 1, wherein said crystallizing is performed in the presence of sodium hydroxide.

* * * * *